(12) United States Patent
Zandhuis

(10) Patent No.: US 8,712,009 B2
(45) Date of Patent: Apr. 29, 2014

(54) CAN SEAM INSPECTION

(75) Inventor: Johannes Albertus Zandhuis, Kings Norton (GB)

(73) Assignees: Heinz Grossjohann, Kinderhook, NY (US); Alexis Grossjohann, Delmar, NY (US)

( * ) Notice: Subject to any disclaimer, the term of this patent is extended or adjusted under 35 U.S.C. 154(b) by 576 days.

(21) Appl. No.: 12/864,406

(22) PCT Filed: Jan. 20, 2009

(86) PCT No.: PCT/GB2009/000156
§ 371 (c)(1),
(2), (4) Date: Mar. 14, 2011

(87) PCT Pub. No.: WO2009/093015
PCT Pub. Date: Jul. 30, 2009

(65) Prior Publication Data
US 2011/0150316 A1    Jun. 23, 2011

(30) Foreign Application Priority Data

Jan. 24, 2008 (GB) .................................. 0801307.0
Sep. 17, 2008 (GB) .................................. 0817009.4

(51) Int. Cl.
*G01B 15/06* (2006.01)
(52) U.S. Cl.
USPC .................. 378/58; 378/55; 378/62; 382/152
(58) Field of Classification Search
USPC .......... 356/445; 378/15, 50, 61, 63, 113, 150; 382/113, 128, 131; 600/407
See application file for complete search history.

(56) References Cited

U.S. PATENT DOCUMENTS

| | | | | |
|---|---|---|---|---|
| 3,852,600 A | * | 12/1974 | Faulkner et al. | 378/61 |
| 4,365,339 A | * | 12/1982 | Pavkovich et al. | 378/15 |
| 4,442,535 A | * | 4/1984 | Ishijima et al. | 378/50 |
| 4,644,573 A | * | 2/1987 | Palermo et al. | 378/15 |
| 4,989,225 A | | 1/1991 | Gupta et al. | |
| 4,998,268 A | * | 3/1991 | Winter | 378/63 |
| 5,615,279 A | * | 3/1997 | Yoshioka et al. | 382/131 |
| 5,794,499 A | | 8/1998 | Nakajima et al. | |
| 6,219,402 B1 | | 4/2001 | Beierling | |

(Continued)

FOREIGN PATENT DOCUMENTS

DE   10 2005 062065    7/2007
GB        2215834       9/1989

OTHER PUBLICATIONS

Gueudre C et al. "Geometric characterizations of a circumferential seam by automatic segmentation of digitized radioscopic images" NDT & E International, Butterwirtg-Heinemann< Oxfordm GB< vol. 30, No. 5, Oct. 1, 1997.

(Continued)

*Primary Examiner* — Vikkram Bali
*Assistant Examiner* — Xuemei Chen
(74) *Attorney, Agent, or Firm* — Cozen O'Connor

(57) ABSTRACT

A method of determining integrity of a can seam including disposing the can seam between an X-ray source and an X-ray detector, exposing an overlap region of the can seam to radiation from the source, and determining an indication of integrity of the overlap region from a measure of variation in radiation intensity readings taken by the detector over a series of circumferential intervals of the can seam.

25 Claims, 9 Drawing Sheets

(56) References Cited

U.S. PATENT DOCUMENTS

| | | | |
|---|---|---|---|
| 6,501,828 B1* | 12/2002 | Popescu | 378/150 |
| 6,953,933 B1 | 10/2005 | Ogiso | |
| 7,970,102 B2* | 6/2011 | Gilevich et al. | 378/57 |
| 2006/0044564 A1* | 3/2006 | Draayer et al. | 356/445 |
| 2006/0094950 A1* | 5/2006 | Ning | 600/407 |
| 2011/0013748 A1* | 1/2011 | Ichizawa et al. | 378/113 |
| 2011/0142301 A1* | 6/2011 | Boroczky et al. | 382/128 |
| 2011/0274243 A1* | 11/2011 | Lenko | 378/58 |

OTHER PUBLICATIONS

Hongjun Chen et al., "Application of Visual Servoing to an X-ray Based Welding Inspection Robot" Control and Automation, 2005ICCA. '05. International Conference on Budapest, Hungary Jun. 26-29, 2005, Piscataway< NJ USA, IEEE, vol. 2, Jun. 15, 2005.

* cited by examiner

CAN SEAM INSPECTION

PRIORITY CLAIM

This is a U.S. national stage of Application No. PCT/GB2009/000156, filed on Jan. 20, 2008, which claims priority to Great Britain Application No's: 2008 000 1307, filed: Jan. 24, 2008 and 2008 001 7009, filed Sep. 17, 2008, the contents of all which are incorporated herein by reference.

BACKGROUND OF THE INVENTION

1. Field of the Invention

The invention relates to inspection of can seams by analyzing transmission of radiation, and in particular to a method of assessing the integrity of a can seam.

2. Related Art

Cans, such as those used for packaging food products, require adequate and uniform sealing. Typically, cans are three parts, a top, a bottom circular cover plate, and a cylindrical body section. Sealing of the top and bottom plates to the body section can be achieved by a double seam, wherein the edges of the plate and body are bent around one another to form (ideally) a hermetic seal. Such a double seam is shown schematically in cross-section in FIG. 1.

Can seam 100, having a seam width SW, is formed by an edge of top or bottom plate 103 bent around the edge of the body section 102. The body section bends to form a body hook BH, and the cover plate bends to form a cover hook CH. The can seam 100 is formed having a total external width W. Where the edges overlap, an overlap region OL is defined. An upper clearance UC and a lower clearance LC is defined by the width of the overlap region OL. Typically, the overlap region OL determines the sealing properties of the can. If an overlap region OL is not adequately formed, which may be due to a number of reasons including manufacturing defects, the sealing properties of the can seam can be compromised. The product within the can may then be at risk of putrefaction.

Since the integrity of can seams is of critical importance, methods of inspection have been developed. A conventional method of assessment is by visual observation of a cross-section of a seam, which would typically involve obtaining a cross-section of similar appearance to that shown in FIG. 1. Such a method can determine, for example, the degree of overlap, i.e. the length of the overlap region OL. An alternative method involves sectioning the seam across a plane parallel to the cover plate, in an attempt to reveal the extent of seal in the overlap region OL around the can seam circumference. These conventional methods are, however, time consuming, require destruction of the can seam, may be hazardous to the operator due to sharp cutting edges, and cannot reliably and automatically assess the integrity of a can seam. Such destructive methods also inevitably alter the state of the seam itself during preparation, through the release of internal stresses, and may therefore not produce an accurate picture of the state of the seam prior to the assessment being made.

Non-destructive methods of assessing can seam integrity have consequently been developed. One such method is disclosed in GB 2215834, which describes a method of inspection using X-ray analysis of a can seam. An X-ray beam is directed across the can seam to determine the length of the overlap region, through measuring a variation in transmitted radiation intensity across the width of the seam. An alternative disclosed method involves directing an X-ray beam tangentially across the can seam, and processing an image obtained from the analysis to obtain a cross-sectional view of the can seam. Both these methods aim to determine the quality of the seam through analysis of the overlap region, and in particular the width of the overlap region OL shown in FIG. 1. A measure of the whole of the can seam can be made by rotating the can relative to the X-ray beam and taking a succession of images.

U.S. Pat. No. 6,953,933 discloses further methods of determining the integrity of can seams by X-ray analysis, in which a measure of a size of a space between multiple layers of a can is obtained by scanning an X-ray beam across the can. An intensity distribution curve is obtained from which the dimensions of the can are determined.

Previous solutions to determining integrity of can seams, either through manual destructive methods or by non-destructive X-ray analysis methods, have certain drawbacks. One significant such drawback is that these methods have difficulty in determining the overall integrity of the can seam. If a sufficient width of overlap region exists around the seam, the integrity of the seam is largely determined by the uniformity of contact between the body section 102 and cover plate 103 in the overlap region OL. A sectional view, for example of the form shown in FIG. 1, or a plan view through the width of the can seam, is able to provide indications of the width of the overlap region OL, but not how uniform the contact between the body section 102 and cover plate 103 is around the circumference of the can seam. The term 'free space' is conventionally used in the canning industry to describe the amount of the overlap region OL in which there is not an intimate contact between the body section 102 and the cover plate 103. Increasing amounts of free space lead eventually to failure of the can seam. Currently free space can only be estimated by measuring across the seam, for example by determining the can seam width SW, and subtracting the known thickness of the metal sheet material. This is, however, not accurate. There is therefore a need for an improved method of determining free space.

It is an object of the invention to address one or more of the above mentioned problems.

SUMMARY OF THE INVENTION

In one embodiment, the invention provides a method of determining integrity of a can seam, the method comprising: disposing the can seam between an X-ray source and an X-ray detector; exposing an overlap region of the can seam to radiation from the source; and determining an indication of integrity of the overlap region from a measure of variation in radiation intensity readings taken by the detector over a series of circumferential intervals of the can seam.

In one embodiment, the invention provides an apparatus to determine the integrity of a can seam, the apparatus comprising: an X-ray source; an X-ray detector; a measurement platform configured to locate a can having a can seam between the X-ray source and the X-ray detector to expose an overlap region of the can seam to radiation from the source; and a computing device configured to receive readings from the X-ray detector and control operation of the X-ray source and the measurement platform, wherein the computing device is configured to determine an indication of integrity of the overlap region from a measure of variation in radiation intensity readings taken by the detector over a series of circumferential intervals of the can seam.

In one embodiment, the invention provides a computer program product, comprising a computer readable medium having thereon computer program code means adapted, when said program is loaded onto a computer, to make the computer execute the procedure of the invention of the first aspect.

BRIEF DESCRIPTION OF THE FIGURES

The invention will now be described by way of example, and with reference to the enclosed drawings in which.

DETAILED DESCRIPTION OF THE FIGURES

Figure 1:
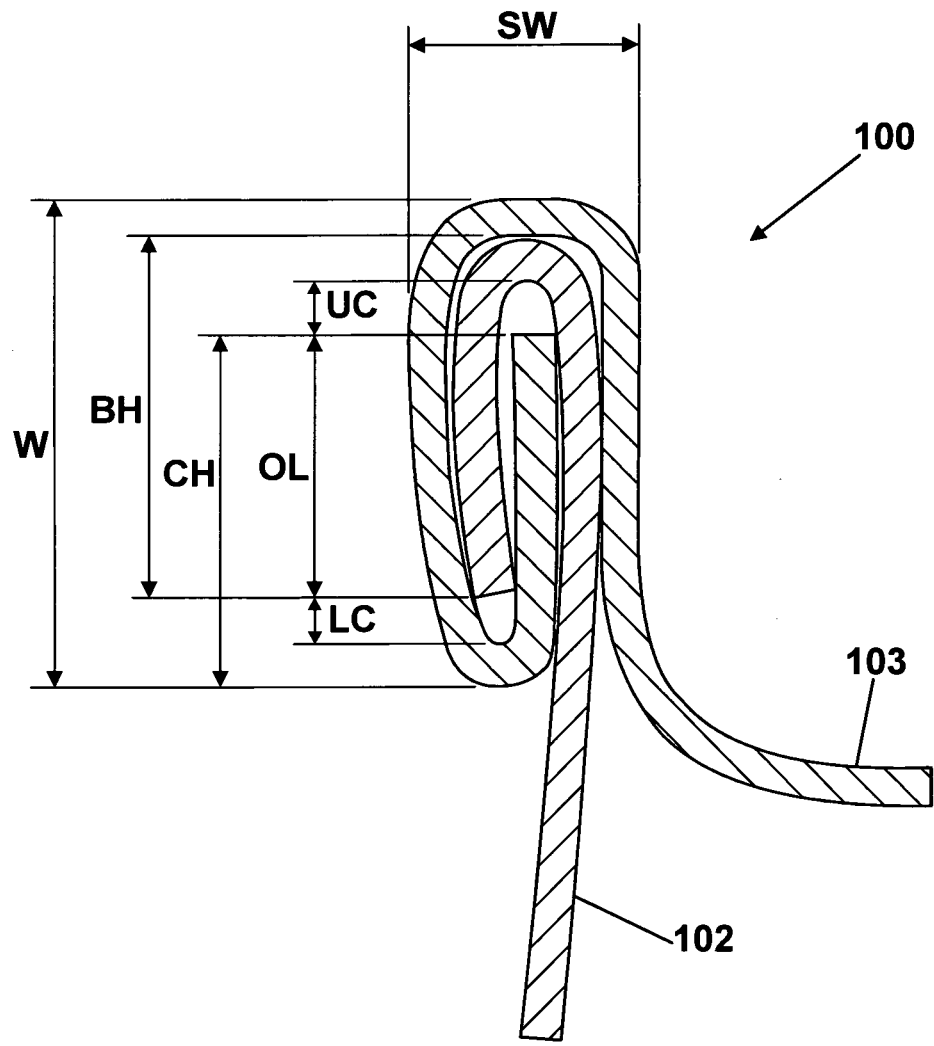
FIG. 1 is a cross-sectional of a can seam.

FIG. 1 has already been discussed above in relation to the cited documents.

Figure 2:
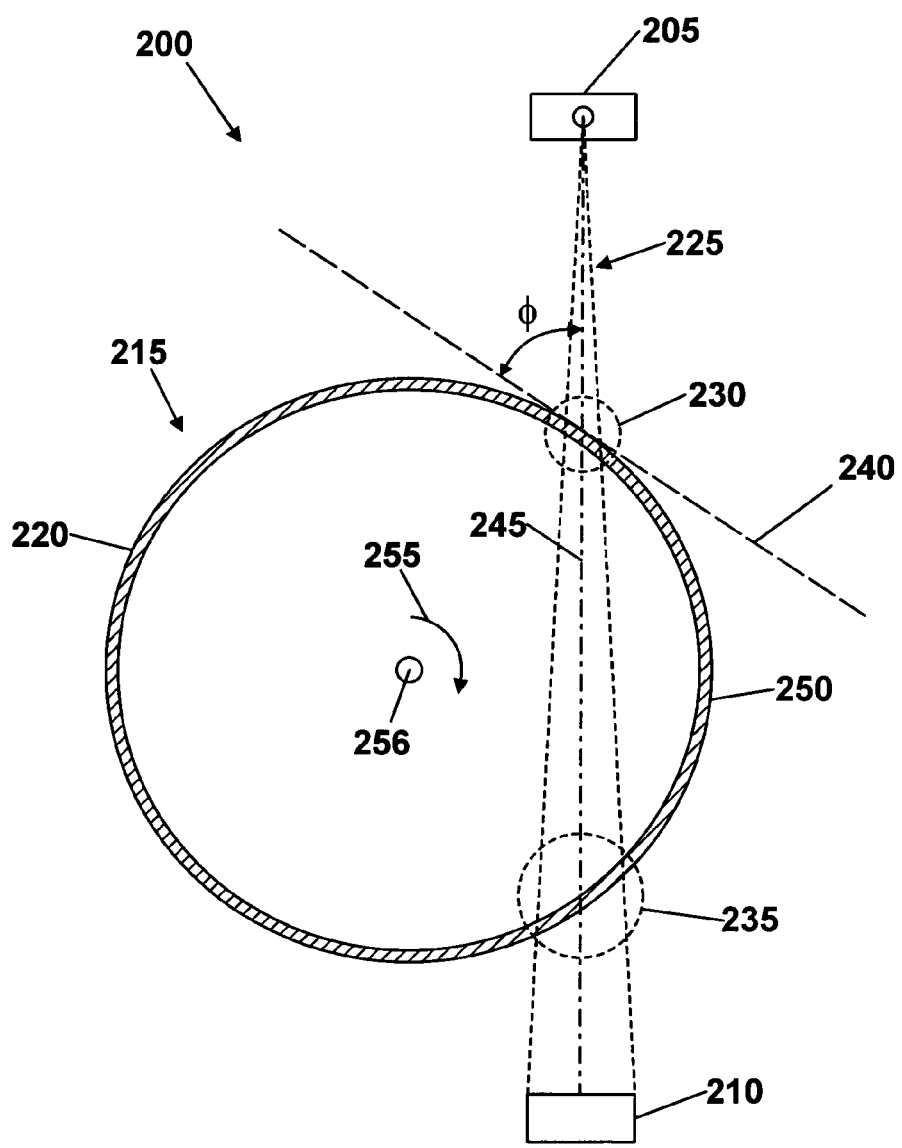
FIG. 2 is a schematic top view representation of an apparatus arranged to measure an integrity of a can seam.

FIG. 2 is a schematic representation of an apparatus 200 arranged to perform a method according to the invention. An X-ray source 205 and X-ray detector 210 are disposed either side of a can 215 on a measurement platform, the can being shown in cross-section to illustrate the can seam 220 to be analyzed. The can 215 shown is circular in cross-section. Other cross-sectional shapes may be analyzed without departing from the scope of the invention. FIG. 2 emphasizes an X-ray geometry whereby the X-ray source or spot 205 is disposed outside an outer periphery 250 of the can seam 220. An alternative geometry is also possible whereby the spot 205 is placed inside the outer periphery 250 of the can seam 220, described below in relation to FIGS. 6a and 6b.

A beam 225, emitted from the source 205, extends between the source 205 and the detector 210, the beam 225 passing through the can seam 220. It is to be understood that the beam 225 may be arranged to pass through the can seam 220 in one or two regions 230, 235 by arrangement of the tilt of the beam 225 relative to the plane of the cover plate of the can. The source 205 and detector 210 arrangement is preferably tilted so that the beam 225 passes through only one of the regions 230, 235 of the can seam 220. Which region is chosen may depend on the width of the beam and the type of detector, determining how much of the can seam is to be analyzed in one measurement. The detector 210 may be an area detector, i.e. configured to provide a reading of radiation intensity over a two-dimensional area covering the can seam or a portion thereof. The detector 210 may alternatively be a line detector, configured to provide a one-dimensional reading of radiation intensity across the can seam. Such a line detector is preferably oriented generally parallel to a longitudinal axis 256 of the can 215, the longitudinal axis 256 being defined by the cylindrical portion of the can 215. Other orientations may be possible.

A tangent line 240 is shown in FIG. 2, which touches the outer circumference 250 of the can seam 220 at a point where a line 245 between the source 205 and the detector 210 crosses the outer circumference 250 of the can seam 220. The line 245 may, for example, be the central axis of the beam 225 formed by the X-ray source 205. An angle is thereby formed between the tangent line 240 and the beam line 245. As will be explained below, the angle is preferably such that it is possible to determine, from a variation in radiation intensity taken over a series of circumferential intervals of the can seam 220, the integrity of the can seam 220, and in particular the integrity of the overlap region of the can seam 220.

In FIG. 2, a series of circumferential intervals is represented by the width of the beam 225 as the beam 225 passes through the can seam 220, through the first or second regions 230, 235 of the can seam 220. Alternatively, a series of circumferential intervals may be represented by a series of measurements taken by the detector, when in the form of a line detector, in which the can 215 is rotated 255, about the longitudinal axis 256 of the can 215, relative to the detector 210 between each measurement. Measurements may be possible while continuously or intermittently performing such relative rotation, optionally including mechanical scanning of the detector 210. Of course, rotation 255 of the can 215 relative to the detector 210 may be achieved either by physically rotating the can 215 or by rotating the X-ray source 205 and detector 210 relative to the can 215, both achieving the same effect.

Figure 3:
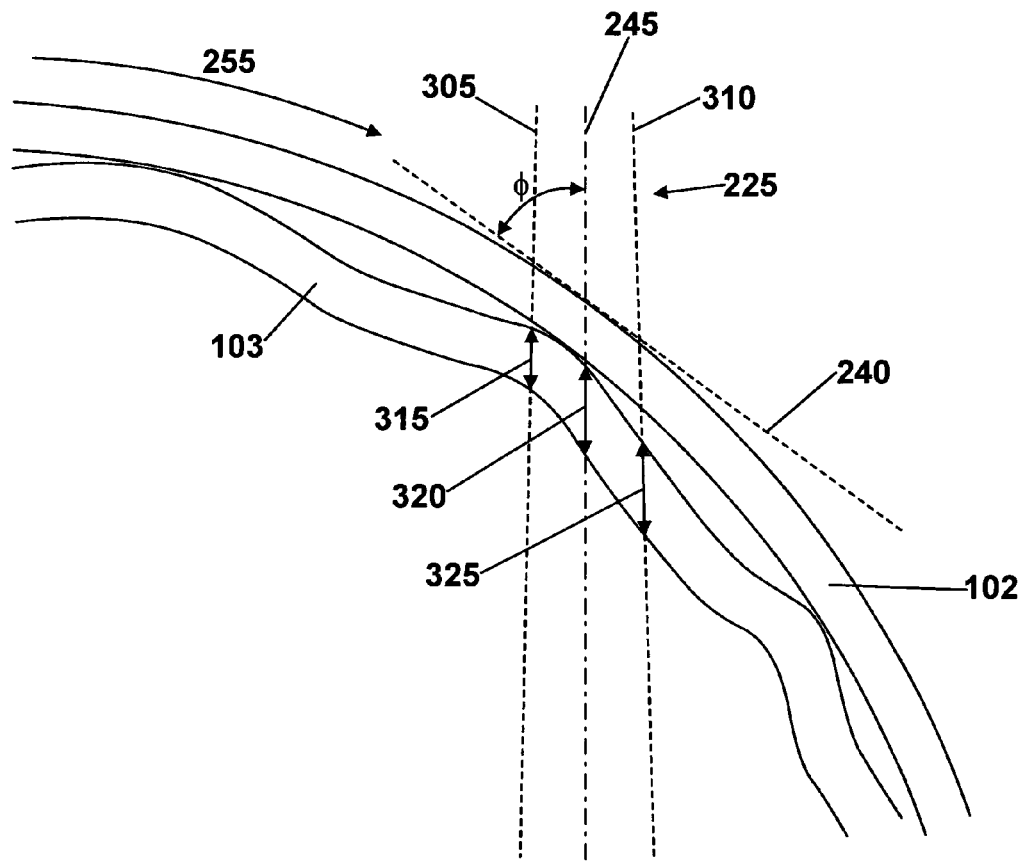
FIG. 3 shows a schematic top view cross-sectional representation of an overlap region of a can seam.

FIG. 3 illustrates a schematic cross-sectional representation of an overlap region of the first region 230 of the can seam 220 of FIG. 2. A center line 245 of the beam 225 passes through the overlap region comprising edges of the cover plate 103 and the body section 102. A manufacturing defect is shown, exaggerated to more readily illustrate the effect of the invention, in the form of undulations in the cross-section of the edge of the cover plate 103. Such undulations can arise because the cover plate 103 is bent around a greater distance than the body section 102, as is evident from considering FIG. 1, because the edge of the cover plate is bent from a greater starting diameter, while the edge of the body section 102 is bent to only a slightly larger diameter. This can result in warping, or wrinkling, of the edge of the cover plate 103, if the manufacturing parameters are not adequately controlled. Wrinkles may not, however, be evident at all from an external inspection of the can seam. The warping may also not be immediately evident from performing X-ray inspections using the previous methods outlined in the above cited documents. Previously, a method of analyzing such a defect would require sectioning of the can seam parallel to the cover plate to reveal the section represented in FIG. 3, in a process known as a 'pull-down'. In such a process, the seam is cut apart and manually disassembled, requiring operator skill and care when working with sharp edges and tools. Wrinkles will tend to show up as a widening of the seam width SW (FIG. 1) because there is more 'free space' inside the seam. To measure this requires knowledge of the thickness of the sheet metal used, which can vary. The methods described herein provide ways of giving more direct indications of the amount of free space in the seam.

The beam 225, represented by the center line 245 and a left and right extremity 305, 310, passes through a series of circumferential intervals of the can seam 220. The beam 225 passes through a similar thickness of the body section 102 at each interval, due to the edge of the body section 102 being uniform and the total angle subtended by the beam being relatively small.

The beam 225 passes through a first thickness 315 of the cover plate 103 at the first interval, a second thickness 320 at a second interval and a third thickness 325 at a third interval. As can be seen from the Figure, the thickness varies as a function of the interval due to how the cover plate 103 is warped relative to the body section 102. Readings of radiation transmission for each of the intervals will consequently vary accordingly, with a low intensity reading being adjacent to or bounded by regions of relatively high intensity, corresponding to undulations in the cover plate 103.

A single 'snapshot' reading taken with an X-ray beam 245 and an area detector 210 could be sufficient to detect whether the cover plate 103 is warped such that the overlap region is compromised. An area detector 210 could thereby measure the variation in radiation intensities over a series of circumferential intervals of the can seam in a single reading. Preferably a series of measurements are taken, between which the can is rotated relative to the detector 210 and the source 205. This will allow a larger overall picture to be built up of the distribution of such defects, if present, in the can seam 220. Alternatively, if a line detector is used, a series of readings taken at different circumferential intervals by rotating the can relative to the detector will be required to build up the overall picture. In both cases, however, the line 245 between the detector 210 and source 205 preferably remains at a consistent angle ø relative to the tangent 240 at the point where the line 245 crosses the outer circumference 250 of the can seam 220. In the former situation, where an area detector is used, the angle of intersection between the beam 225 and the can seam 220 varies around this angle ø due to the angle subtended by the beam 225, whereas in the latter situation where a line detector is used, the angle of intersection is constant and equal to the angle ↑ between the tangent 240 and the beam line 245.

In the case of a line detector oriented orthogonally to the axis 256 of the can 215, the line detector (or can) may be scanned mechanically in a direction parallel to the axis 256, to build up a picture of the can seam width. If a point detector is used, the detector may be scanned mechanically in directions both parallel and orthogonal to the axis 256 to build up each picture of the can seam width.

Preferably the angle ø lies between 20 and 70 degrees. More preferably, the angle ø lies between 40 and 50 degrees. A preferred value for the angle ø is around 45 degrees.

In a general aspect applying to each of the above situations, the integrity of the overlap region is determined from a measure of variation in radiation intensity readings taken by the detector 210 over a series of circumferential intervals of the can seam 220.

Figure 4:
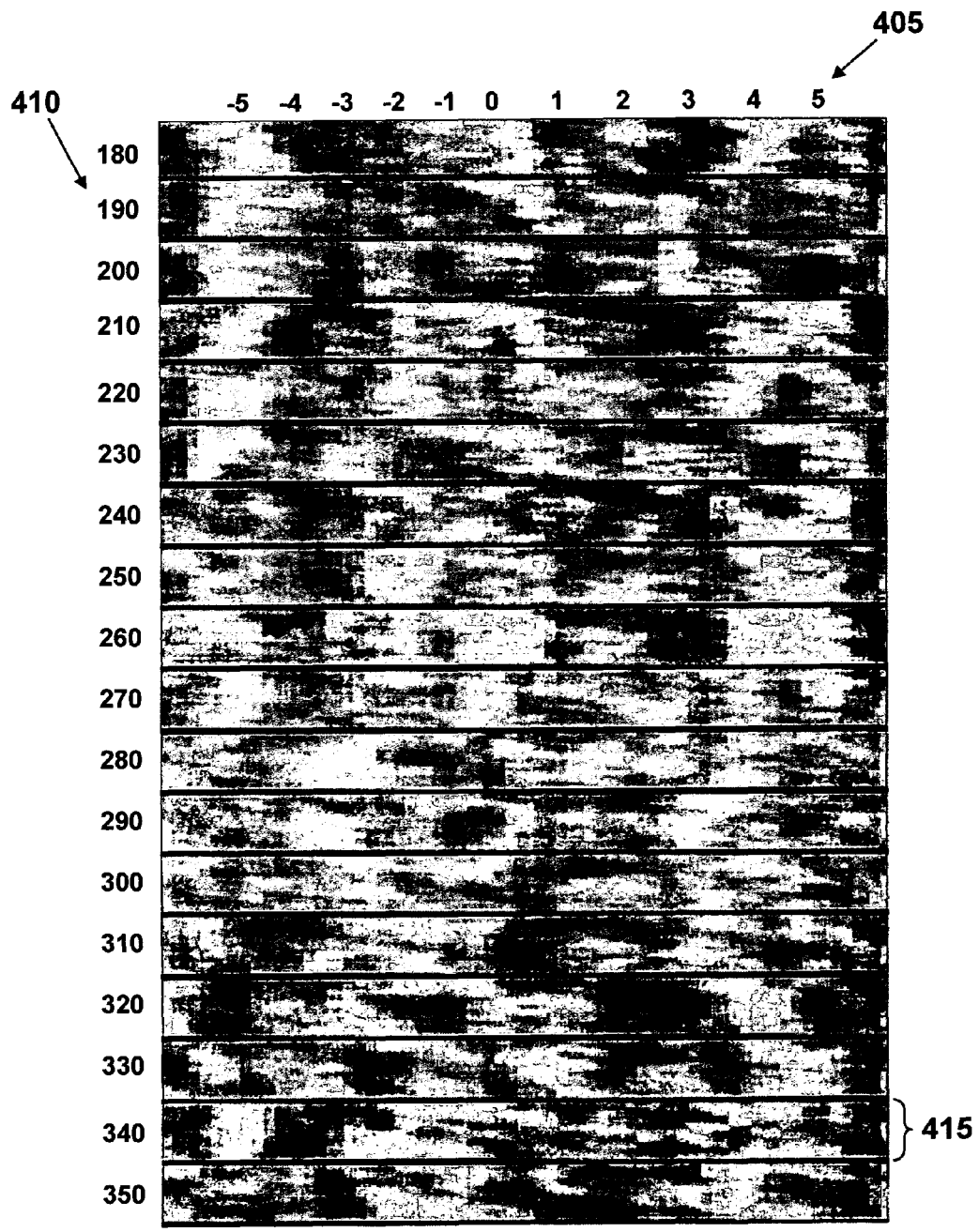
FIG. 4 is an exemplary analysis of a well-sealed can seam.

FIG. 4 shows a set of exemplary results from analysis of a well-sealed can seam. The results are presented in the form of a series of measurements, each measurement 415 representing a two-dimensional 'snapshot' taken over the subtended angle of an X-ray beam of the overlap region of a can seam. The vertical axis 410 represents relative rotation between the can and the detector/source (in degrees) between each measurement, which varies from 180 to 350 degrees in 10 degree intervals. Within each measurement 415, the vertical axis represents position through the overlap region of the can seam, i.e. in a direction parallel to the can axis 256. The horizontal axis 405 represents the angle of the beam away from a central axis of the beam, which in this case varies from around +6 to −6 degrees (i.e. a total subtended angle of around 12 degrees), with readings along the axis shown from +5 to −5 degrees, corresponding to different circumferential positions.

As can be seen in FIG. 4, because the can seam is well-sealed there is little variation in the intensity readings along both the vertical and horizontal axes.

Figure 5:
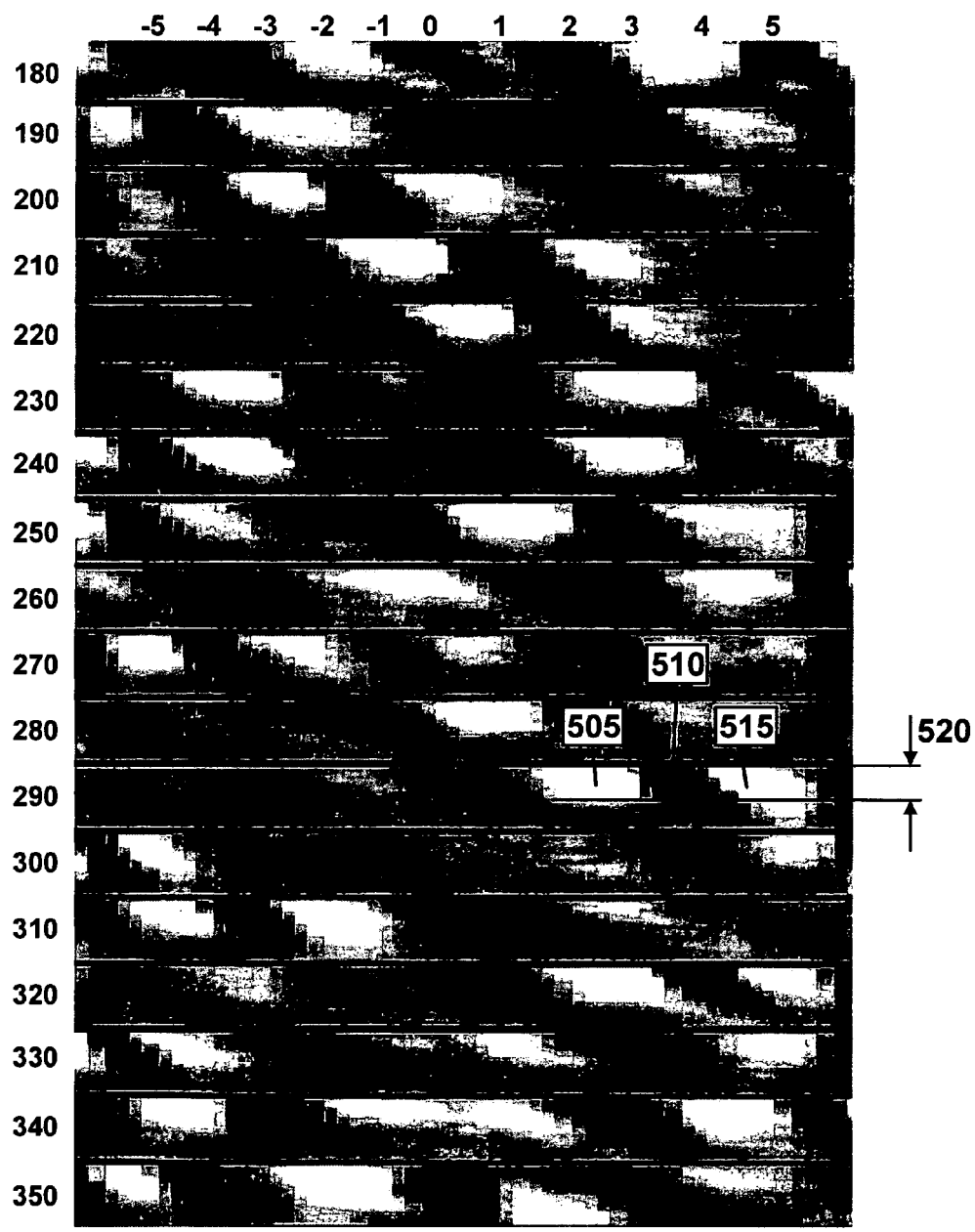
FIG. 5 is an exemplary analysis of a poorly-sealed can seam.

Shown in FIG. 5 is a similar set of measurements, with the same axes represented, on a can seam known to be defective. In this case, the variation in radiation intensity over both the horizontal and the vertical axes is clear and striking. Taking the variation across the horizontal axis, several regions can be seen in which a dark area 510 (representing a lower degree of radiation transmission) is bounded on either side by bright areas 505, 515 (representing a higher degree of transmission). These regions consequently indicate that the overlap region is compromised by warping of the cover plate, as illustrated above in relation to FIG. 3.

Also observable from the results shown in FIG. 5 is the extent to which the warping affects the integrity of the overlap region. Because the two-dimensional measurements taken produce readings of radiation intensity across the overlap region as well as around the circumference of the can seam, the proportion of the overlap region, indicated by the average extent 520 of the regions affected, that is considered to be sealed can be determined. In this case, the percentage of overlap is around 50%, i.e. 50% of the overlap is functioning as an adequate seal. The results shown in FIG. 4, by contrast, illustrate a 100% overlap seal, because no evidence of warping can be seen. Through automated analysis of results such as those shown in FIGS. 4 and 5, an indication of the degree of overlap present in the can seam can be reliably determined.

Methods of automating analysis of such measurements may include computing a series of indications of variation in transmitted radiation through the overlap region for each series of circumferential intervals. The variation in transmitted radiation, as illustrated in FIG. 5, provides an indication of whether, and to what extent, wrinkling is present. The indication of variation may be obtained by any of a number of ways, including calculating deviation about a mean value of radiation intensity, for example by determining an effective RMS (root mean square) value for each series of circumferential intervals. Alternatively, an indication of the maximum deviation from an overall mean value may provide the required indication. The latter will provide the 'worst case' for a set of readings, while the former will provide an overall average picture. Other statistical methods of determining variation about a mean may be used, such as calculations of variance or standard deviation. Taking a set of calculated readings across the width of the overlap region, and around at least a representative proportion of the circumference of the can seam, will allow a measurement of the percentage overlap to be taken for the can seam being analyzed. The ultimate result of the analysis method may therefore be a simple numerical indication of the quality of the can seam, for example in percentage terms. A clear 'pass/fail' indication can be provided to an operator, or to a production control or quality system such as a statistical process control (SPC) system. An operator provided with such an indication would not therefore need to be highly skilled in interpreting results such as those shown in FIGS. 4 and 5.

Implementations of the invention will typically include a computing device (e.g. a general purpose computer) configured and programmed to control operation of a measurement platform on which a can to be analyzed is positioned. The computing device may be configured to operate the source 205 and detector 210, to process readings received from the detector 210, and provide indications such as those shown in FIGS. 4 and 5 to an operator, for example via a display. The computing device may also be programmed to automatically determine from the readings one or more of the indications mentioned above, derived from variations in radiation intensity. The computing device may be configured to operate the measurement platform to rotate the can as required, taking a series of measurements between which the can seam 220 is rotated relative to the detector.

Figure 6A:
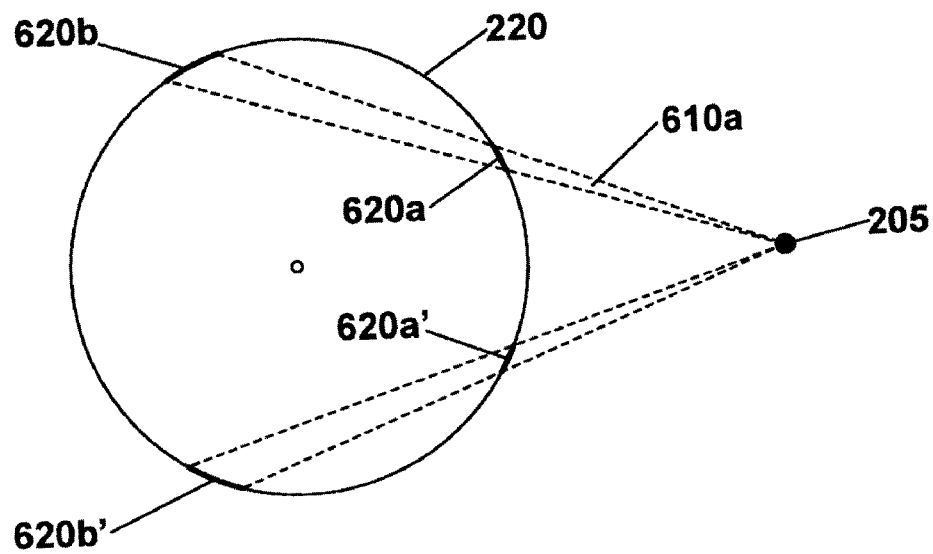
FIGS. 6a and 6b are a difference in can seam section illumination between alternative measurement geometries.
Figure 6B:
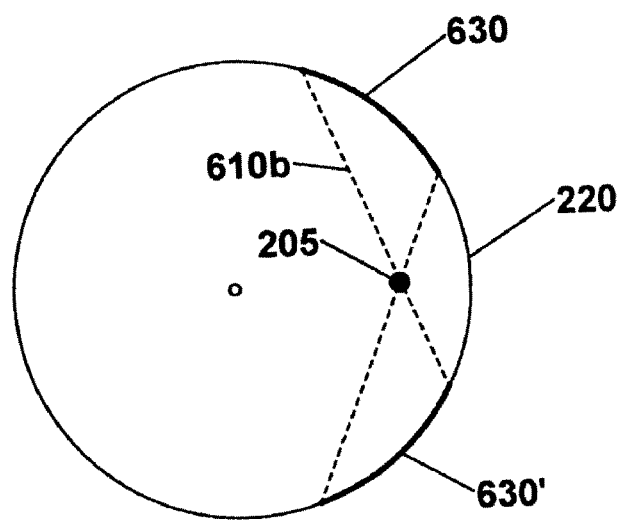

An advantage of the invention as described above is that an analysis method is obtained that can be completely automated, for example as part of a production line, and can provide clear and simple indications as part of a quality control procedure on filled cans without the need for destructive testing. As mentioned above, an alternative geometry to that illustrated in FIG. 2 is possible where the X-ray source 205 is situated inside the outer periphery 250 of the can seam 220. One benefit of using this alternative 'inside-out' geometry over the 'outside-in' geometry shown in FIG. 2 is illustrated schematically in FIGS. 6a and 6b. Constraining the beam 610a, 610b in each case to intersect the can seam 220 close to a preferred angle, in this case around 45 degrees, FIGS. 6a and 6b illustrate a large difference in the extent of the seam section illuminated in one 'snapshot' of the can seam 220. While the 'outside-in' geometry shown in FIG. 6a shows small sections 620a, 620b and 620a', 620b' being illuminated, the 'inside-out' geometry shown in FIG. 6b shows much larger sections 630, 630' illuminated within the same limits of intersection angle between the X-ray beam 610 and the can seam 220. The 'inside-out' geometry of FIG. 6b can therefore allow inspection of a larger seam section, therefore requiring fewer shots to inspect the whole seam, resulting in a higher throughput.

Multiple detectors, for example taking measurements simultaneously at different locations around the can seam 220, may alternatively be used, which can also speed up the throughput.

Figure 7:
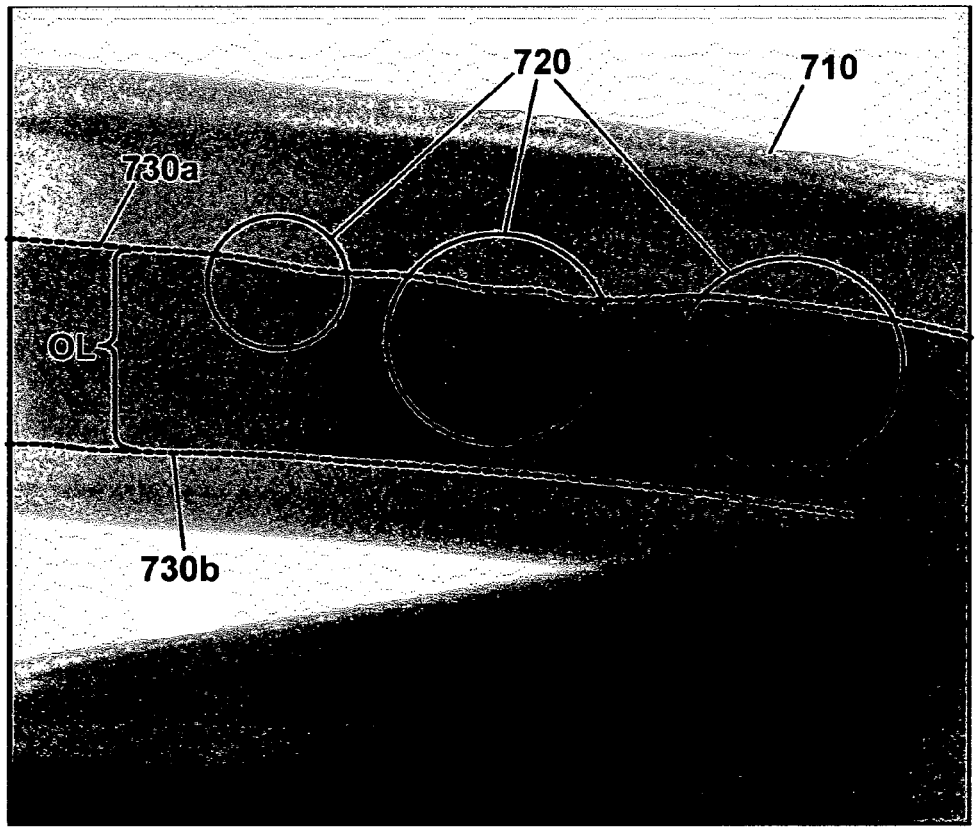
FIG. 7 is an exemplary X-ray transmission image through a can seam.

FIG. 7 illustrates an exemplary X-ray transmission image taken through a can seam 710. Variations in thickness of metal through which the X-ray beam travels are indicated as variations in brightness in the X-ray image, with darker regions indicating a greater thickness of metal. The overlap region OL, where the thickness of metal is greatest, is indicated by a darker band, highlighted in FIG. 7 between upper and lower bounds 730a, 730b superimposed on the image. Regions 720 of differing contrast are highlighted, indicating possible wrinkles in the overlap region. These regions are, however, not prominent in the raw image. Image processing techniques can be used to extract useful information from the raw image as presented in FIG. 7, in order to emphasize such variations, if present.

Figure 8A:
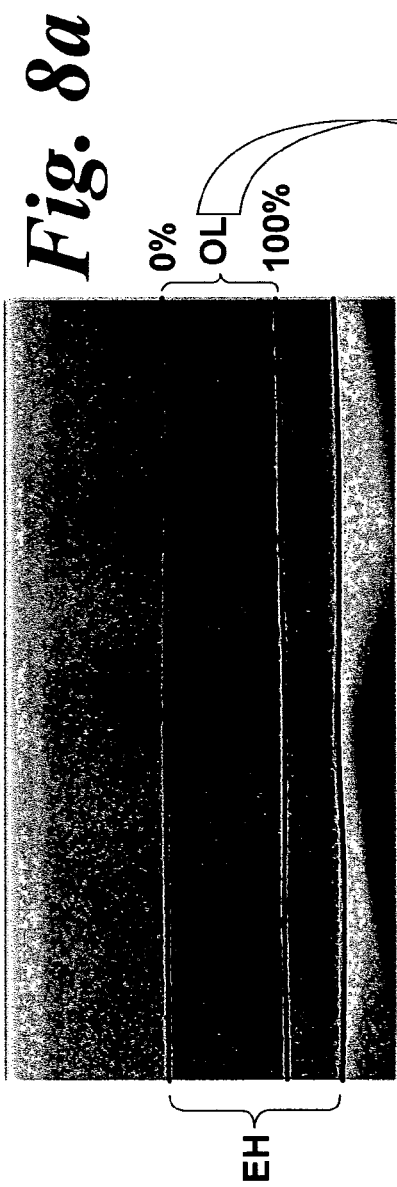
FIGS. 8a-c illustrate exemplary images taken through a seam section of a can with different degrees of image processing.
Figure 8B:
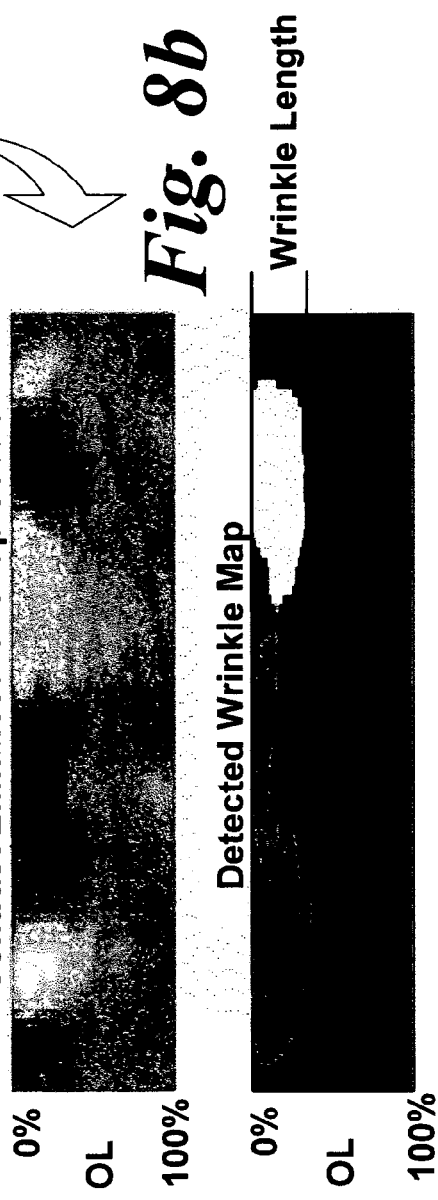
Figure 8C:

FIGS. 8a to 8c illustrate different views of a can seam, taken after applying different image processing methods to the raw X-ray transmission intensity image through the can seam. The raw image of FIG. 7, which necessarily takes a view through the can seam at an oblique angle, may conveniently be straightened to align the overlap region OL of the can seam with an x axis, with vertical sections through the overlap region OL and end hook region EL represented on the y axis. FIG. 8a shows a single captured image taken over a 10 degree interval of the can seam after such a straightening process. Straightening of the image of FIG. 7 can be achieved, for example, by identification of the characteristic pattern of the overlap region OL or by identification of the top edge of the can seam, followed by a conformal mapping process that aligns the identified edge with an axis of the modified image.

Small contrast differences across the overlap region caused by wrinkles can be made more clearly visible by applying a threshold to the radiation intensity information in the images of FIG. 8 a (or alternatively directly to the image of FIG. 7). The pattern of wrinkles in the overlap region can then be made clearer, as shown in FIG. 8b. This image corresponds to one of the sequences of snapshots illustrated in FIGS. 4 and 5. Further analysis of the images can be carried out to determine a calculated extent of the wrinkles, for example in the form of wrinkle length, in the can seam, the result of which is shown in FIG. 8c in the form of a detected 'wrinkle map'.

Due to the change in angle between the X-ray beam and the can seam across each section, a gradual change in apparent thickness will be measured across the can seam. In the raw image shown in FIG. 7, this will be represented as a decrease in brightness from left to right. This change, which is caused by the geometry of the measurement set-up, can be accounted for by applying a curve function to the raw data, together with the offset provided by applying a threshold as described above. The curve function may be derived from the known geometry of the measurement set-up or can be applied using a polynomial curve-fitting function. A fourth-order polynomial function is typically sufficient to approximate the effects of curvature of the can seam as viewed from the detector.

It is to be understood that the images in FIGS. 8 a to 8 c are presented to illustrate aspects of the invention, but are not themselves necessary to perform the invention itself. In practice it would not be necessary to produce such images, except possibly for calibration of the measurement system by an expert user.

Figure 9:
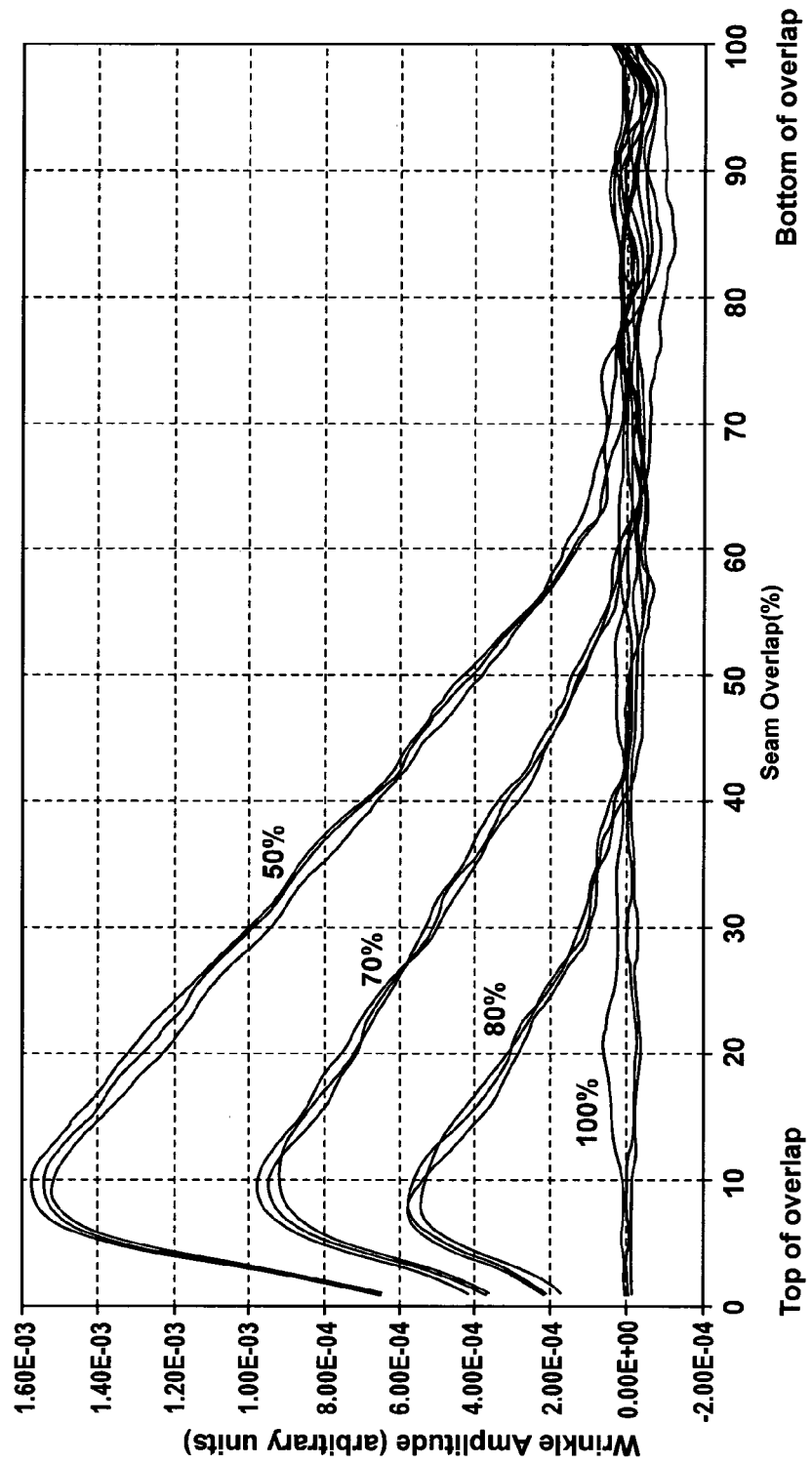
FIG. 9 is a measurement of wrinkle amplitudes derived from X-ray measurements taken through can seams of varying degrees of integrity.

Sequences of images such as those shown in FIG. 7 can be automatically analyzed, and variations in radiation intensity over circumferential intervals of a can seam calculated. These variations may, for example, be in the form of R-MS calculations for different lines of measurement around the can seam across the overlap region. Shown in FIG. 9 are plots of RMS intensity measurements taken from a range of can seams having known different degrees of integrity, ranging from 100% to 50%. FIG. 9 shows the variation in radiation intensity as a function of position through the can overlap (i.e. from top to bottom) for can seams having differing integrity indicated by a 50, 70, 80 and 100% tightness rating. Each measurement was repeated three times for the same can to demonstrate the repeatability of the measurement process. The wrinkle amplitude represented on the y axis is in arbitrary units, and relates to the variation in radiation intensity measured around the can seam, for example as shown in FIG. 8b.

As it can be seen from the curves in FIG. 9, as the can seam integrity decreases the curves change in overall shape and a maximum value for radiation intensity variation, representing wrinkle amplitude, increases. This maximum, which for each of the results shown lies towards the top of the can overlap, is a direct indicator of the integrity of the can seam. For example, a can seam of 50% integrity is shown in FIG. 9 as having a maximum value of between 1.5 and 1.6 $25 \times 10-3$, while a can seam having an integrity of 80% is shown as having a maximum value of between 5 and $6 \times 10-4$ Such a maximum value can therefore be used as a simple test for the integrity of a can seam, thereby reducing the whole measurement process to a single result that can be used to produce a pass or fail indication, depending on a particular threshold value for measured integrity. The maximum value may alternatively be represented by a measured difference between the highest and lowest wrinkle amplitude (i.e. radiation variation) values across the can seam overlap or end hook region. This may be used as a direct measure for the amount of free space in the seam. Since the process of taking measurements and the subsequent image analysis can be automated, the invention allows a relatively unskilled operator to determine whether can seams are meeting the required standard of integrity.

Other embodiments are intentionally within the scope of the invention as defined by the appended claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method of determining integrity of a can seam, comprising:
   disposing the can seam between an X-ray source and an X-ray detector;
   exposing an overlap region of the can seam to radiation from the source;
   measuring a variation in radiation intensity readings taken by the X-ray detector over a series of circumferential intervals of the can seam; and
   determining an indication of integrity of the overlap region from the measure of variation in radiation intensity readings,
   wherein, for each of the radiation intensity readings, an angle of between 20 and 70 degrees is made between a central axis line connecting the X-ray source and the X-ray detector and a tangent to an outer circumference of the can seam at a point where the central axis line crosses the outer circumference,
   whereby a beam from the X-ray source passes through one region of the can seam.

2. The method of claim 1, further comprising rotating the can seam about a can axis relative to the X-ray detector between intensity readings.

3. The method of claim 1, wherein the X-ray detector is an area detector.

4. The method of claim 2, wherein the X-ray detector is a line detector.

5. The method of claim 1, wherein each of the radiation intensity readings is taken with a substantially constant angle between the central axis line connecting the X-ray source and the X-ray detector and the tangent to an outer circumference of the can seam at a point where the central axis line crosses the outer circumference.

6. The method of claim 1, wherein the angle is between 40 and 50 degrees.

7. The method of claim 1, wherein the step of determining further comprises computing a series of indications of variation in transmitted radiation through an overlap region for the series of circumferential intervals.

8. The method of claim 7, wherein the step of determining further comprises computing a maximum value for the variation in transmitted radiation through the overlap region.

9. The method of claim 7, wherein each of the series of indications comprises an RMS (root mean square) value of radiation intensity for the series of circumferential intervals at differing positions across the overlap region.

10. The method of claim 7, wherein each of the series of indications comprises an indication of deviation from a mean value of radiation intensity for the series of circumferential intervals at differing positions across the overlap region.

11. The method of claim 1, wherein the X-ray source is disposed outside an outer perimeter of the can seam.

12. The method of claim 1, wherein the X-ray source is disposed inside an outer perimeter of the can seam.

13. An apparatus to determine can seam integrity, comprising:
   an X-ray source;
   an X-ray detector;
   a measurement platform configured to locate a can having a can seam between the X-ray source and the X-ray detector to expose an overlap region of the can seam to radiation from the source; and
   a computing device configured to:
     receive readings from the X-ray detector and control operation of the X-ray source and the measurement platform and
     determine an indication of integrity of the overlap region from a measure of variation in radiation intensity readings taken by the X-ray detector over a series of circumferential intervals of the can seam,
     wherein, for each of the radiation intensity readings, the computing device is configured to control the measurement platform such that an angle of between 20 and 70 degrees is made between a central axis line connecting the X-ray source and the X-ray detector and a tangent to a point where the central axis line crosses an outer circumference of the can seam,
     whereby a beam from the X-ray source passes through one region of the can seam.

14. The apparatus of claim 13 wherein the computing device is configured to take the intensity readings in a series of measurements between which the can seam is rotated relative to the X-ray detector.

15. The apparatus of claim 13, wherein the X-ray detector is an area detector.

16. The apparatus of claim 14, wherein the X-ray detector is a line detector.

17. The apparatus of claim 13, wherein the computing device is configure do take each of the radiation intensity readings with a consistent angle between the central axis line connecting the X-ray source and the X-ray detector and a tangent to a point where the central axis line crosses an outer circumference of the can seam.

18. The apparatus of claim 17, wherein the angle is between 40 and 50 degrees.

19. The apparatus of claim 13, wherein the computing device is configured to calculate a series of indications of variations in transmitted radiation through an overlap region for the series of circumferential intervals.

20. The apparatus of claim 19 wherein the computing device is configured to calculate a maximum value for the variation in transmitted radiation through the overlap region.

21. The apparatus of claim 19, wherein each of the series of indications comprises an RMS (root mean square) value of radiation intensity for the series of circumferential intervals at differing positions across the overlap region.

22. The apparatus of claim 19 wherein each of the series of indications comprises an indication of deviation from a mean value of radiation intensity for the series of circumferential intervals at differing positions across the overlap region.

23. The apparatus of claim 13, wherein the X-ray source is disposed outside an outer perimeter of the can seam.

24. The apparatus of claim 13, wherein the X-ray source is disposed within an outer perimeter of the can seam.

25. A computer program product, comprising:
   a nontransient computer readable medium having thereon computer program code, when said program is loaded onto a computer, to make the computer execute a method comprising:

activating an X-ray source to expose an overlap region of a can seam, disposed between the X-ray source and an X-ray detector, to radiation from the source;

measuring a variation in radiation intensity readings taken by the X-ray detector over a series of circumferential intervals of the can seam;

determining an indication of integrity of the overlap region from the measure of variation in radiation intensity readings; and control, for each of the radiation intensity readings, a measurement platform such that an angle of between 20 and 70 degrees is made between a central axis line connecting the X-ray source and the X-ray detector and a tangent to a point where the central axis line crosses an outer circumference of the can seam, whereby a beam from the X-ray source passes through one region of the can seam.

* * * * *